United States Patent
Schroeder et al.

(10) Patent No.: US 8,697,044 B2
(45) Date of Patent: Apr. 15, 2014

(54) CROSSED-LINKED HYALURONIC ACID AND COLLAGEN AND USES THEREOF

(75) Inventors: Jacqueline A. Schroeder, Boulder Creek, CA (US); Gregory S. Dapper, Newark, CA (US); Kenneth C. Olson, Foster City, CA (US)

(73) Assignee: Allergan, Inc., Irvine, CA (US)

( * ) Notice: Subject to any disclaimer, the term of this patent is extended or adjusted under 35 U.S.C. 154(b) by 905 days.

(21) Appl. No.: 12/247,175

(22) Filed: Oct. 7, 2008

(65) Prior Publication Data

US 2009/0093755 A1 Apr. 9, 2009

Related U.S. Application Data

(60) Provisional application No. 60/978,423, filed on Oct. 9, 2007.

(51) Int. Cl.
*A61F 2/02* (2006.01)
*A61M 5/178* (2006.01)
*A61L 27/54* (2006.01)

(52) U.S. Cl.
USPC ............ 424/78.3; 424/423; 424/422; 604/57; 623/23.72

(58) Field of Classification Search
None
See application file for complete search history.

(56) References Cited

U.S. PATENT DOCUMENTS

| | | | |
|---|---|---|---|
| 2,128,827 A | 8/1938 | Killian | |
| 3,548,056 A | 12/1970 | Eigen et al. | |
| 3,763,009 A | 10/1973 | Suzuki | |
| 3,949,073 A | 4/1976 | Daniels et al. | |
| 4,060,081 A | 11/1977 | Yannas et al. | |
| 4,140,537 A | 2/1979 | Luck et al. | |
| 4,233,360 A | 11/1980 | Luck et al. | |
| 4,273,705 A | 6/1981 | Kato | |
| 4,279,812 A | 7/1981 | Cioca | |
| 4,282,954 A | 8/1981 | Hill | |
| 4,424,208 A | 1/1984 | Wallace et al. | |
| 4,501,306 A | 2/1985 | Chu et al. | |
| 4,582,640 A | 4/1986 | Smestad et al. | |
| 4,582,865 A | 4/1986 | Balazs et al. | |
| 4,605,691 A * | 8/1986 | Balazs et al. ............ | 524/27 |
| 4,636,524 A | 1/1987 | Balazs | |
| 4,642,117 A | 2/1987 | Nguyen et al. | |
| 4,713,448 A | 12/1987 | Balazs | |
| 4,716,154 A | 12/1987 | Malson et al. | |
| 4,803,075 A * | 2/1989 | Wallace et al. ............ | 424/423 |
| 4,886,787 A | 12/1989 | De Belder et al. | |
| 4,896,787 A | 1/1990 | Delamour et al. | |
| 5,009,013 A | 4/1991 | Wiklund | |
| 5,087,446 A | 2/1992 | Suzuki et al. | |
| 5,091,171 A | 2/1992 | Yu et al. | |
| 5,143,724 A | 9/1992 | Leshchiner et al. | |
| 5,246,698 A | 9/1993 | Leshchiner et al. | |
| 5,314,874 A * | 5/1994 | Miyata et al. ............ | 514/17.2 |
| 5,328,955 A | 7/1994 | Rhee et al. | |
| 5,356,883 A | 10/1994 | Kuo et al. | |
| 5,399,351 A | 3/1995 | Leshchiner et al. | |
| 5,428,024 A * | 6/1995 | Chu et al. ............ | 514/17.2 |
| 5,531,716 A | 7/1996 | Luzio et al. | |
| 5,565,519 A | 10/1996 | Rhee et al. | |
| 5,571,503 A | 11/1996 | Mausner | |
| 5,614,587 A | 3/1997 | Rhee et al. | |
| 5,616,568 A | 4/1997 | Pouyani et al. | |
| 5,616,611 A | 4/1997 | Yamamoto | |
| 5,616,689 A | 4/1997 | Shenoy et al. | |
| 5,633,001 A | 5/1997 | Agerup | |
| 5,643,464 A | 7/1997 | Rhee et al. | |
| 5,676,964 A | 10/1997 | della Valle | |
| 5,716,404 A | 2/1998 | Vacanti | |
| 5,823,671 A | 10/1998 | Mitchell et al. | |
| 5,824,333 A | 10/1998 | Scopelianos et al. | |
| 5,827,529 A | 10/1998 | Ono et al. | |
| 5,843,907 A | 12/1998 | Sakai | |
| 5,880,107 A | 3/1999 | Buenter | |
| 5,886,042 A | 3/1999 | Yu et al. | |
| 5,935,164 A | 8/1999 | Iversen | |
| 5,972,385 A | 10/1999 | Liu et al. | |
| 5,980,930 A | 11/1999 | Fenton et al. | |
| 6,013,679 A | 1/2000 | Kuo et al. | |
| 6,066,325 A | 5/2000 | Wallace et al. | |
| 6,129,761 A | 10/2000 | Hubbell | |

(Continued)

FOREIGN PATENT DOCUMENTS

| | | |
|---|---|---|
| CA | 949965 | 6/1974 |
| EP | 0273823 | 12/1987 |
| EP | 0416250 | 3/1991 |
| EP | 0416846 | 3/1991 |
| EP | 1247522 | 10/2002 |
| EP | 141792 | 4/2003 |
| EP | 1398131 | 3/2004 |
| EP | 1532991 | 5/2005 |
| EP | 1726299 | 11/2006 |
| EP | 2236523 | 10/2010 |

(Continued)

OTHER PUBLICATIONS

McClelland, Plastic Reconstructive Surg., 100, 1997.*
Aesthetic Buyers Guide, Juvederm Raises Stardards, Jan./Feb. 2007, pp. 5. www.miinews.com.
McPherson et al., Development and Biochemical Characterization of Injectable Collagen, J. Dermatol Surg Oncol, 1988, 14, Supp 1.
Rehakova, Milena, et al., "Properties of collagen and hyaluronic acid comosite materials and their modification by chemical crosslinking," Journal of Biomedical Research, vol. 30, 1996, pp. 369-372, XP002590342.

(Continued)

*Primary Examiner* — Robert A Wax
*Assistant Examiner* — William Craigo
(74) *Attorney, Agent, or Firm* — Linda Fox (57) ABSTRACT

The present invention discloses a cross-linked hyaluronic acid/collagen formulation which has improved composition for dermal filling and higher persistence than cross-linked collagen or HA alone. Also disclosed are methods for preparing cross-linked hyaluronic acid/collagen formulations and using such for augmenting soft tissues in mammals.

30 Claims, 6 Drawing Sheets

(56) References Cited

U.S. PATENT DOCUMENTS

| | | |
|---|---|---|
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2* | 9/2005 | Spiro et al. ............ 424/488 |
| 6,979,440 B2 | 12/2005 | Shefer et al. |
| 6,991,652 B2 | 1/2006 | Burg |
| 7,119,062 B1 | 10/2006 | Alvis et al. |
| 7,129,209 B2 | 10/2006 | Rhee |
| 7,166,570 B2 | 1/2007 | Hunter et al. |
| 7,192,984 B2 | 3/2007 | Berg et al. |
| 7,196,180 B2 | 3/2007 | Aeschlimann |
| 7,314,636 B2 | 1/2008 | Caseres et al. |
| 7,316,822 B2 | 1/2008 | Binette |
| 7,491,709 B2 | 2/2009 | Carey |
| 7,741,476 B2 | 6/2010 | Lebreton |
| 7,767,452 B2 | 8/2010 | Kleinsek |
| 7,799,767 B2 | 9/2010 | Lamberti et al. |
| 7,875,296 B2 | 1/2011 | Binette |
| 7,902,171 B2 | 3/2011 | Reinmuller et al. |
| 8,053,423 B2 | 11/2011 | Lamberti et al. |
| 8,124,120 B2 | 2/2012 | Sadozai |
| 8,137,702 B2 | 3/2012 | Binette et al. |
| 8,153,591 B2 | 4/2012 | Masters et al. |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1* | 7/2004 | Zhao et al. ............ 536/53 |
| 2004/0199241 A1 | 10/2004 | Gravett et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0226936 A1 | 10/2005 | Agerup |
| 2005/0271729 A1 | 12/2005 | Wang |
| 2005/0287180 A1 | 12/2005 | Chen |
| 2006/0040894 A1 | 2/2006 | Hunter et al. |
| 2006/0095137 A1 | 5/2006 | Chung et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1* | 12/2006 | Tsuchiya et al. ............ 438/458 |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1* | 8/2008 | Kitazono et al. ............ 424/488 |
| 2008/0200430 A1 | 8/2008 | Bitterman et al. |
| 2008/0207794 A1 | 8/2008 | Wright et al. |
| 2008/0241252 A1 | 10/2008 | Lyons |
| 2008/0268051 A1 | 10/2008 | Lyons |
| 2008/0274946 A1 | 11/2008 | Giampapa |
| 2008/0279806 A1 | 11/2008 | Cho |
| 2008/0293637 A1 | 11/2008 | Schroeder et al. |
| 2009/0018102 A1 | 1/2009 | Moutet et al. |
| 2009/0022808 A1 | 1/2009 | Champion |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder et al. |
| 2009/0098177 A1 | 4/2009 | Werkmeister et al. |
| 2009/0110671 A1 | 4/2009 | Miyata et al. |
| 2009/0110736 A1 | 4/2009 | Boutros |
| 2009/0123547 A1 | 5/2009 | Hill et al. |
| 2009/0124552 A1 | 5/2009 | Hill et al. |
| 2009/0143331 A1 | 6/2009 | Stroumpoulis et al. |
| 2009/0143348 A1 | 6/2009 | Tezel |
| 2009/0148527 A1 | 6/2009 | Robinson |
| 2009/0155314 A1 | 6/2009 | Tezel et al. |
| 2009/0155362 A1 | 6/2009 | Longin |
| 2009/0162415 A1 | 6/2009 | Huang et al. |
| 2009/0169615 A1 | 7/2009 | Pinsky |
| 2009/0263447 A1 | 10/2009 | Asius et al. |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0255068 A1 | 10/2010 | Stroumpoulis et al. |
| 2010/0316683 A1 | 12/2010 | Piron |
| 2011/0034684 A1 | 2/2011 | Yokokawa |
| 2011/0070281 A1 | 3/2011 | Altman |
| 2011/0077737 A1 | 3/2011 | Stroumpoulis et al. |
| 2011/0097381 A1 | 4/2011 | Binette |
| 2011/0118206 A1 | 5/2011 | Lebreton |
| 2011/0150823 A1 | 6/2011 | Huang |
| 2011/0171286 A1 | 7/2011 | Cecile et al. |
| 2011/0171311 A1 | 7/2011 | Gousse et al. |
| 2011/0172180 A1 | 7/2011 | Gousse et al. |
| 2011/0224164 A1 | 9/2011 | Lebreton |
| 2011/0229574 A1 | 9/2011 | Guillen et al. |
| 2012/0010146 A1 | 1/2012 | Han et al. |
| 2012/0034462 A1 | 2/2012 | Stroumpoulis et al. |
| 2012/0071437 A1 | 3/2012 | Stroumpoulis et al. |
| 2012/0076868 A1 | 3/2012 | Lamberti et al. |
| 2012/0156265 A1 | 6/2012 | Binette et al. |
| 2012/0164098 A1 | 6/2012 | Schroeder et al. |
| 2012/0172328 A1 | 7/2012 | Lebreton |
| 2012/0189589 A1 | 7/2012 | Van Epps et al. |
| 2012/0189590 A1 | 7/2012 | Van Epps et al. |
| 2012/0189591 A1 | 7/2012 | Van Epps et al. |
| 2012/0189699 A1 | 7/2012 | Stroumpoulis et al. |
| 2012/0189708 A1 | 7/2012 | Van Epps et al. |
| 2012/0208890 A1 | 8/2012 | Gousse et al. |

(56) References Cited

U.S. PATENT DOCUMENTS

| | | | |
|---|---|---|---|
| 2012/0225842 A1 | 9/2012 | Cecile et al. |
| 2012/0232030 A1 | 9/2012 | Gousse et al. |
| 2012/0295870 A1 | 11/2012 | Lebreton |

FOREIGN PATENT DOCUMENTS

| | | |
|---|---|---|
| FR | 2733427 | 5/2001 |
| FR | 2920000 | 2/2009 |
| FR | 2924615 | 1/2010 |
| JP | 55-153711 | 11/1980 |
| JP | 2007063177 | 3/2007 |
| WO | WO 86/00079 | 1/1986 |
| WO | WO 86/00912 | 2/1986 |
| WO | WO 92/00105 | 1/1992 |
| WO | WO 92/20349 | 11/1992 |
| WO | WO 94/01468 | 1/1994 |
| WO | WO 94/02517 | 2/1994 |
| WO | WO 96/33751 | 1/1996 |
| WO | WO 97/04012 | 2/1997 |
| WO | WO 98/35639 | 8/1998 |
| WO | WO 98/35640 | 8/1998 |
| WO | WO 00/01428 | 1/2000 |
| WO | WO 01/79342 | 10/2001 |
| WO | WO 02/05753 | 1/2002 |
| WO | WO 02/06350 | 1/2002 |
| WO | WO 02/09792 | 2/2002 |
| WO | WO02/17713 A1 | 3/2002 |
| WO | WO 03/007782 | 1/2003 |
| WO | WO 2004/020473 | 3/2004 |
| WO | WO 2004/022603 | 3/2004 |
| WO | WO 2004/073759 | 9/2004 |
| WO | WO 2004092223 A1 * | 10/2004 |
| WO | WO 2005040224 A1 * | 5/2005 |
| WO | WO 2005/067994 | 7/2005 |
| WO | WO 2005/074913 | 8/2005 |
| WO | WO 2005/112888 | 12/2005 |
| WO | WO 2006/023645 | 3/2006 |
| WO | WO 2006/067608 | 6/2006 |
| WO | WO 2007/018124 | 2/2007 |
| WO | WO2007/070617 A1 | 6/2007 |
| WO | WO 2007/077399 | 7/2007 |
| WO | 2007136738 | 11/2007 |
| WO | WO 2007/128923 | 11/2007 |
| WO | WO 2008/034176 | 3/2008 |
| WO | WO 2008/068297 | 6/2008 |
| WO | WO 2008/072230 | 6/2008 |
| WO | WO 2008/077172 | 7/2008 |
| WO | WO 2008/098019 | 8/2008 |
| WO | WO 2008/139122 | 11/2008 |
| WO | WO 2008/148967 | 12/2008 |
| WO | WO2008/157608 A1 | 12/2008 |
| WO | WO 2009/024719 | 2/2009 |
| WO | WO 2009/026158 | 2/2009 |
| WO | WO 2009/028764 | 3/2009 |
| WO | WO 2009/034559 | 3/2009 |
| WO | WO 2009/073437 | 6/2009 |
| WO | WO 2010/003797 | 1/2010 |
| WO | WO 2010/015900 | 2/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |
| WO | 2011072399 | 6/2011 |

OTHER PUBLICATIONS

Millay et al.; "Vasoconstrictors in Facial Plastic Surgery"; Archives of Otolaryngology—Head & Neck Surgery; vol. 117; pp. 160-163; Feb. 1991.

Wahl, "European Evaluation of a New Hyaluronic Acid Filler Incorporating Lidocaine", Journal of Cosmetic Dermatology; vol. 7; pp. 298-303; 2008.

Adams; "An Analysis of Clinical Studies of the Uses of Crosslinked Hyaluronan, Hylan, in the Treatment of Osteoarthritis"; J. Rheumatol Suppl. ; vol. 39; pp. 16-18; Aug. 1993.

Allemann et al.; "Hyaluronic acid gel (JUVADERM) preparations in the treatment of facial wrinkles and folds"; Clinical Interventions in Aging; vol. 3, No. 4; pp. 629-634; 2008.

Bluel et al.; "Evaluation of Reconstituted Collagen Tape as a Model for Chemically Modified Soft Tissues", Biomat. Med. Dev. Art. Org.; vol. 9(1); pp. 37-46; 1981.

Capozzi et al., "Distant Migration of Silicone Gel From a Ruptured Breast Implant", Plastic and Reconstructive Surgery; vol. 62; pp. 302-303; 1978.

Champion et al., "Role of Target Geometry in Phagocytosis"; S. Proc. Nat. Acad. Sci.; vol. 103; No. 13; pp. 4930-4934; Mar. 28, 2006.

Chvapil, "Collagen Sponge: Theory and Practice of Medical Applications", J. Biomed Mater. Res., vol. II, pp. 721-741; 1977.

Clark et al., "The Influence of Triamcinolone Acetonide on Joint Stiffness in the Rat", J Bone Joint Surg; vol. 53-A; pp. 1409-1414; Oct. 1971.

Cohen et al., "Organization and Adhesive Properties of the Hyaluronan Pericellular Coat of Chrondrocytes and Epithelial Cells", Biophys J.; vol. 85; pp. 1996-2005; Sep. 2003.

Deland, "Intrathecal Toxicity Studies with Benzyl Alcohol", Toxicol Appl Pharmacol; vol. 25; pp. 153-156; 1973.

Eyre et al., Top Curr. Chem., vol. 247, pp. 207-229; 2005.

Grecomoro et al., "Intra-Articular Treatment with Sodium Hyaluronate in Gonarthosis: A Controlled Clinical Trial Versus Placebo", Pharmatherapeutica, vol. 5(2); pp. 137-141; 1987.

Grillo et al., "Thermal Reconstitution of Collagen from Solution and the Response to Its Heterologous Implantation", JSR; vol. II, No. 1, pp. 69-82; Jan. 1962.

Hayashibara, "AA2G"; Sep. 23, 2007, http://web.archive.org/web/20079230720l0/http://www.hayashibara-intl.com/cosmetics/aa2g.html.

Helliwell, "Use of an Objective Measure of Articular Stiffness to Record Changes in Finger Joints After Intra-Articular Injection of Corticosteroid", An Theum Dis; vol. 56; pp. 71-73; 1997.

Hertzberger-Ten Cate et al., "Intra-Articular Steroids in Pauciarticular Juvenile Chronic Arthritis", Type I, Eur J Pediatr; vol. 150; pp. 170-172; 1991.

Hetherington, "Potential for Patient Harm From Intrathecal Administration of Preserved Solutions", Abstract only Med J; vol. 173(3); p. 141; Aug. 2000.

Hurst, "Adhesive Arachnoiditis and Vascular Blockage Caused by Detergents and Other Chemical Irritants: an Experimental Study", J Path Bact, vol. LXX, No. 70; pp. 167-177; 1955.

Jones et al., "Intra-Articular Hyaluronic Acid Compared to Intra-Articular Triamcinolone Hexacetonide in Inflammatory Knee Osteoarthritis", Osteoarthritis Cartilage, vol. 3; pp. 269-273; 1995.

Klein, "Skin Filling Collagen and Other Injectables of the Skin", Dermatologic Clinics; vol. 19, No. 3, pp. 491-588; Jul. 2001.

Kopp et al., "The Short-Term Effect of Intra-Articular Injections of Sodium Hyaluronate and Corticosteroid on Temporomandibular Joint Pain and Dysfunction"; J. Oral Maxillofac Surg.; V. 43; pp. 429-435; 1985.

Laeschke, "Biocompatibility of Microparticles into Soft Tissue Fillers", Semin. Cutan. Med. Surg., vol. 23; pp. 214-217; 2004.

Mancinelli et al., "Intramuscular High-Dose Triamcinolone Acetonide in the Treatment of Severe Chronic Asthma", West J. Med; vol. 167(5); pp. 322-329; Nov. 1997.

McCarty et al., "Inflammatory Reaction After Intrasynovial Injection of Microcrystalline Adrenocorticosteroid Esters", Arthritis and Rheuymatism; vol. 7(4); pp. 359-367; 1964.

Remington's Pharmaceutical Science Mac Publishing Company, Easton, Pa 16th Edition 1980; 1- page.

Rosenblatt et al., "The Effect of Collagen Fiber Size Distribution on the Release Rate of Proteins from Collagen Matrices by Diffusion", J. Controlled Rel., vol. 9; pp. 195-203; 1989.

(56) References Cited

OTHER PUBLICATIONS

Rosenblatt et al., "Chain Rigidity and Diffusional Release in Biopolymer Gels", Proceed. Inter. Symp. Control. Rel. Bioact. Mater.; vol. 20; pp. 264-265; 1993; Controlled Release Society, Inc.
Selvi et al, "Arthritis Induced by Corticosteroid Crystals", J. Rheumatology; vol. 34:3; 1 page; 2004.
Zulian et al., "Triamcinolone Acetonide and Hexacetonide Intra-Articular Treatment of Symmetrical Joints in Juvenile Idiopathic Arthritis: a Double-Blind Trial", Rheumatology; vol. 43; No. 10; pp. 1288-1291; 2004.
Powell; "Stability of Lidocaine in Aqueous Solution: Effect of Temperature, pH, Buffer, and Metal Ions on Amide Hydrolysis"; Pharmaceutical Research; vol. 4, No. 1, 1987.
Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.
Lindvall et al.; "Influence of Various Compounds on the Degradation of Hyaluronic Acid by a Myeloperoxidase System"; Chemcio-Biological Interactions; vol. 90; pp. 1-12; 1994.
Weidmann; "New Hyaluronic Acid Filler for Subdermal and Long-Lasting Volume Restoration of the Face"; European Dermatology; pp. 65-68; 2009.
Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.
Buck et al, "Injectable Fillers for our Facial Rejuvenation: a Review", Journal of Plastic, Reconstructive and Aesthetic Surgery, (2009), 62:11-18, XP002668828.
Park et al., "Biological Characterization of EDC-crosslinked Collagen-Hyaluronic Acid Matrix in Dermal Tissue Restoration", Biomaterials 24 (2003) 1631-1641.
Park et al., "Characerization of Prous Collagen/Hyaluronic Acid Scaffold Modified by 1-ethyl-3-(3-dimethylaminopropyl)carbodiimide cross-linking", Biomaterials 23 (2002): 1205-1212.
Albano, Emanuele, et al., "Hyroxyethyl Radicals in Ethanol Hepatotoxicity," Frontiers in Bioscience 4:533-540 (1999).
Antunes, Alberto A., et al., "Efficacy of Intrarectal Lidocaine Hydrochloride Gel for Pain control in Patients Undergoing Transrectal Prostate Biopsy", International Braz J Urol, vol. 30(5): 380-383, Sep.-Oct. 2004.
Atanassoff, Peter G., et al., "The Effect of Intradermal Administration of Lidocaine and Morphine on the Response to Thermal Stimulation", Anesth Analg 1997; 84:1340-3.
Baumann et al. "JUVEDERM vs. ZYPLAST Nasolabial Fold Study Group, Comparison of smooth-gel hyaluronic acid dermal fillers with cross-linked bovine collagen: a multicenter, double-masked, randomized, within-subject study." Dermatol. Surg. 33(Suppl 2): S128-S135 (2007).
Beasley et al. :Hyaluronic acid fillers: a comprehensive review. Facial Plast. Surg. 25(2): 86-94 (2009).
Beer "Dermal fillers and combinations of fillers for facial rejuvenation." Dermatol. Clin. 27(4): 427-432 (2009).
Belda, Jose I., et al., "Hyaluronic acid combined with mannitol to improve protection against free-radical endothelial damage: Experimental Model," J.Cataract Refract Surg 2005; 31:1213-1218.
Bircher, Andreas J., et al., "Delayed-type hypersensitivity to subcutaneous lidocaine with tolerance to articaine: confirmation by in vivo and in vitro tests", Contact Dermatitis 1996, 34, 387-389.
Carlin, G., et al., "Effect of anti-inflammatory drugs on xanthine oxidase and xanthine oxidase induced depolymerization of hyaluronic acid," Agents and Actions. 16 (5):377-384 (1985).
Carruthers et al. "The science and art of dermal fillers for soft-tissue augmentation." J. Drugs Dermatol. 8(4): 335-350 (2009).
Chin, Thomas M., et al., "Allergic Hypersensitivity to Lidocaine Hydrochloride", International journal of Dermatology, vol. 19, Apr. 1980, pp. 147-148.
Desai et al., J. Pharm Sci Feb. 1995; 84 (2): 212-5.

Falcone et al. "Crosslinked hyaluronic acid dermal fillers: a comparison of rheological properties." J Biomed Mater Res A. 87(1): 264-271 (2008).
Falcone et al. "Temporary polysaccharide dermal fillers: a model for persistence based on physical properties." Dermatol Surg. 35(8): 1238-1243 (2009).
Farley, Jon S., et al., "Diluting Lidocaine and Mepivacaine in Balanced Salt Solution Reduces the Pain of Intradermal Injection", Regional Anesthesia 19(1):48-51, 1994.
Frati, Elena, et al., "Degradation of hyaluronic acid by photosensitized riboflavin in vitro. Modulation of the effect by transition metals, radical quenchers, and metal chelators," Free Radical Biology Medicine 22 (7):1139-1144 (1997).
Fujinaga, Masahiko, et al., "Reproductive and Teratogenic Effects of Lidocaine in Sprague-Dawley Rats", Anesthesiology 65:626-632, 1986.
Gammaitoni, Arnold R., et al., "Pharmacokinetics and safety of continuously applied lidocaine patches 5%", Am J Health Syst Pharm, vol. 59, Nov. 15, 2002, pp. 2215-2220.
GinShiCel MH Hydroxy Propyl Methyl Cellulose, Web Page http://www.ginshicel.cn/MHPC.html, Nov. 12, 2008.
Gold MH, "Use of Hyaluronic acid fillers for the treatment of the aging face." Clin. Interventions Aging 2(3): 369-376 (2007).
Goldberg "Breakthroughs in US dermal fillers for facial soft-tissue augmentation." J Cosmet Laser Ther. 11(4): 240-247 (2009).
Graefe, Hendrik, et al., "Sensitive and specific photometric determination of mannitol in human serum," Clin Chem Lab Med. 41 (8):1049-1055 (2003).
Hassan et al., Effects of Adjuvants to local anaesthetics on their duration. III. Experimental studies of hyaluronic acid. Abstract Pub Med [Acta Anesthesiol Scand. May 1985; 29(4):384-8].
Intramed Mannitol 20% m/v Infusion, package insert, pp. 1-2 (2010) http://home.intekom.com/pharm/intramed/manit120.html.
Kablik et al. "Comparative physical properties of hyaluronic acid dermal fillers." Dermatol. Surg. Suppl. 35(Suppl. 1): 302-312 (2009).
Kulicke et al., "Visco-Elastic Properties of Sodium Hyaluronate Solutions," American Institue of Physics (2008).
Lamar et al., "Antifibrosis Effect of Novel Gels in Anterior Ciliary Slerotomy *ACS)," ARVO 2002 abstract.
Levy, Jaime et al., "Lidocaine hypersensitivity after subconjunctival injection", Can J Ophthalmol 2006; 41:204-6.
Lupo, MP., "Hyaluronic acid fillers in facial rejuvenation." Semin. Cutan. Med. Surg. 25(3): 122-126 (2006).
Mackley, et al., "Delayed-Type Hypersensitivity to Lidocaine", Arch Dermatol, vol. 139, Mar. 2003, pp. 343-346.
Matsumoto, Alan H, et al., "Reducing the Discomfort of Lidocaine Administration through pH Buffering," Journal of Vascular and Interventional Radiology, Jan.-Feb. 1994, pp. 171-175.
Orvisky, E., et al., "High-molecular-weight hyaluronan—a valuable tool in testing the antioxidative activity of amphiphilic drugs stobadine and vinpocetine," Pharm.Biomed.Anal. 16:419-424 (1997).
Osmitrol (generic name Mannitol),Official FDA Information, side effects and uses, pp. 1-10 (2010) http://www.drugs.com/pro/osmitrol.html.
Prestwich, Glenn D., "Evaluating drug efficacy and toxicology in three dimensions: using synthetic extracellular matrices in drug discovery," Accounts of Chemical Research 41 (1):139-148 (2008).
Sannino et al., "Crosslinking of Cellulose Derivatives and Hyaluronic Acid with Water-Soluble Carbodiimide," Polymer 46 (2005)pp. 11206-11212.
Sculptra® Aesthetic (injectable poly-L-lactic acid) Directions for Use, Dermik Laboratories product insert.
Segura et al. "Crosslinked hyaluronic acid hydrogels: a strategy to functionalize and pattern." Biomaterials 26(4): 359-371 (2005).
Serban et al. "Modular Extracellular Matrices: Solutions for the Puzzle." Methods 45(1): 93-98 (2008).
Shu et al. "Synthesis and evaluation of injectable, in situ crosslinkable synthetic extracellular matrices for tissue engineering." J. Biomed. Mater. Res. A. 79(4): 902-912 (2006).
Silver et al., "Physical Properties of Hyaluronic Acid and Hydroxypropylmethylcellulose in Solution: Evaluation of Coating Ability," Journal of Applied Biomaterials, vol. 5, 89-98 (1994).

(56) References Cited

OTHER PUBLICATIONS

Smith, Kevin C., et al., "Five Percent Lidocaine Cream Applied Simultaneously to Skin and Mucosa of the Lips Creates Excellent Anesthesia for Filler Injections", Dermatol Surg 2005; 31:1635-1637.
Tezel et al. "The science of hyaluronic acid dermal fillers." J. Cosmet. Laser Ther. 10(1): 35-42 (2008).
TRB Chemedica Ophthalmic Line, VISIOL, product info., pp. 1-2.
VISIOL, Viscoelstic gel for use in ocular surgery, (2010) p. 1, htt://www.trbchemedica.com/index.php/option=com_content&tas.
Waraszkiewicz, Sigmund M., et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, Nov. 1981, pp. 1215-1218.
Xia, Yun et al., "Comparison of Effects of Lidocaine Hydrochloride, Buffered Lidocaine, Diphenhydramine, and Normal Saline After Intradermal Injection", Journal of Clinical Anesthesia 14:339-343, 2002.
Yeom et al. "Effect of Cross-Linking Reagents for Hyaluronic Acid Hydrogel Dermal Fillers on Tissue Augmentation and Regeneration." Bioconjugate Chem., 21(2): 240-247 (2010).
Yui, Nobuhiko, et al., "Inflammation responsive degradation of crosslinked hyaluronic acid gels," Journal of Controlled Release, 22 (1992) pp. 105-116.
Yui, Nobuhiko, et al., "Photo-responsive degradation of heterogeneous hydrogels comprising crosslinked hyaluronic acid and lipid microspheres for temporal drug delivery," Journal of Controlled Release, 26 (1993) pp. 141-145.
Yun, YH et al., "Hyaluronan Microspheres for Sustained Gene Delivery and Site-Specific Targeting.", Biomaterials, vol. 25, 2004, pp. 147-157.
Zheng et al. "In situ crosslinkable hyaluronan hydrogels for tissue engineering." Biomaterials 25(7-8): 1339-1348 (2004).

\* cited by examiner

Figure 4A FT-IR Spectrum of HACgn

Figure 4B FT-IR Spectrum of HAVSCgn

CROSSED-LINKED HYALURONIC ACID AND COLLAGEN AND USES THEREOF

RELATED APPLICATION

This application claims priority to U.S. Provisional Patent Application Ser. No. 60/978,423 filed on Oct. 9, 2007, which is incorporated herein by reference.

FIELD OF THE INVENTION

The present invention relates in general to compositions and methods for producing materials for soft tissue augmentation. More specifically, the invention provides a cross-linked hyaluronic acid (HA) and collagen (Cgn) implant of improved composition and stability ("persistence") for augmenting soft tissue in mammals.

BACKGROUND OF THE INVENTION

Both collagen and HA are naturally found in the skin. Although the collagen:HA ratios vary with age, sun exposure, type of skin, and other factors, matching the skin's composition could have a positive effect on duration and biocompatibility of a dermal filler.

SUMMARY OF THE INVENTION

The present invention relates to cross-linked HA and collagen implants for augmenting soft tissue in mammals. In one aspect, the invention features a method for preparing an implant. The method comprises contacting HA with a cross-linker to allow cross-linking of the HA by the cross-linker, thereby forming a first composition; contacting the first composition with collagen to allow cross-linking of the collagen by the cross-linker, thereby forming a second composition; and contacting the second composition with a HA solution to allow cross-linking of the HA in the solution by the cross-linker, thereby producing an implant.

Many cross-linkers may be used in a method of the invention, including and not limited to divinyl sulfone (VS), 1,4-butanediol diglycidyl ether (BDDE), ultraviolet radiation, gamma radiation, electron beam radiation, and glutaraldehyde. For example, when VS is used as the cross-linker, the concentration of the VS for forming the first composition may be about 500-10,000 ppm, and preferably about 5000 ppm. The cross-linking of HA with VS for forming the first composition may occur at about 50-60° C.

When practicing the method of the invention, the concentration and the pH of the HA for forming the first composition may be about 30 mg/ml or higher and about 9-12, respectively. In some embodiments, the collagen for contacting the first composition is soluble; in some embodiments, the concentration of the collagen for contacting the first composition is about 10-50 mg/ml, preferably about 30 mg/ml; in some embodiments, the pH of the collagen for contacting the first composition is about 2-3; in some embodiments, the collagen for contacting the first composition is type I, II, III, IV, or V collagen, or a combination thereof. In some embodiments, the pH of the second composition is about 6-8, and preferably about 7. The concentration of the HA solution for contacting the second composition may be about 3-15% weight/volume, and preferably about 5-10% weight/volume. The cross-linking of the HA in the solution by the cross-linker may occur at a pH of about 7.0-7.6.

A method of the invention may further comprise contacting the second composition with a local anesthetic agent such as lidocaine. The concentration of the lidocaine may be about 1-7 mg/ml, and preferably about 2.7-3.3 mg/ml, in the implant.

An implant prepared according to a method described above is within the invention. In particular, the present invention provides an implant comprising a core of HA cross-linked by a cross-linker, a middle layer of collagen surrounding and cross-linked by the cross-linker to the core, and an outer layer of HA surrounding and cross-linked by the cross-linker to the collagen layer. As mentioned above, the cross-linker may be VS, BDDE, ultraviolet radiation, gamma radiation, electron beam radiation, or glutaraldehyde. The implant may further comprise about 10 ppm or less of cross-linker not cross-linked to the HA or collagen. In some embodiments, about 5-50% of the amine groups on the collagen are modified by the cross-linker. In some embodiments, the elastic modulus of the implant is higher than about 200 Pascals or the implant may have an extrusion force through a 24 or larger gauge needle of about 50 Newtons or less.

The invention is also directed to an implant prepared by the method described above, wherein the crosslinker is VS or BDDE, wherein the concentration of the VS for forming the first composition is about 500-10,000 ppm, preferably about 5000 ppm, and wherein the cross-linking of the HA by the VS for forming the first composition occurs at about 50-60° C. In some embodiments of the implant prepared by the method described above, the concentration of the HA for forming the first composition is about 30 mg/ml or higher and the pH of the HA for forming the first composition is about 9-12. In some embodiments of the implant prepared by the method described above, the collagen for contacting the first composition is soluble and the concentration of the collagen for contacting the first composition is about 10-50 mg/ml, preferably about 30 mg/ml. In some embodiments of the implant prepared by the method described above, the pH of the collagen for contacting the first composition is about 2-3 and the collagen for contacting the first composition is type I, II, III, IV, or V collagen, or a combination thereof. In some embodiments of the implant prepared by the method described above, the pH of the second composition is about 6-8, preferably about 7. In some embodiments of the implant prepared by the method described above, the concentration of the HA solution for contacting the second composition is about 3-15% weight/volume, preferably about 5-10% weight/volume. In some embodiments of the implant prepared by the method described above, the cross-linking of the HA in the solution by the cross-linker occurs at a pH of about 7.0-7.6.

The present invention also features a packaged product. The product comprises a syringe and a needle. The syringe is loaded with an implant of the invention.

The invention further provides a method for filling voids and defects and increasing tissue volume in a mammal. The method comprises administering to a mammal an implant of the invention. The implant may be administered by intradermal or subcutaneous injection.

The above mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

The present invention is based, at least in part, on the unexpected discovery that HA cross-linked at a high concentration and then coated with collagen and HA produces a long lasting implant. More specifically, the invention relates to HA and collagen cross-linked using VS to formulate a physiologically-matched wrinkle corrector, which is referred to as HAVSCgn.

In general, HA is first cross-linked at a high concentration. The residual cross-linker is then reacted with collagen followed by the addition of a HA solution for complete utilization of the cross-linker and a laminating effect. The resulting gel has a high elastic modulus yet can still be extruded through a fine gauge needle with minimal force. The HA and collagen combination mimics the natural components of the skin and is an ideal composition for augmenting soft tissue in mammals. The HA and collagen gel of the present invention has improved rheological properties and volume stability or persistence compared to a single component formulation of HA, such as Captique™, or a single component formulation of collagen, such as CosmoPlast®.

The process of the present invention involves obtaining HA either in solid or liquid form and cross-linking HA as a concentrated solution, followed by the addition of collagen and finally more HA. The collagen of the present invention primarily derives from mammalian source materials, such as bovine or porcine corium or tendon or human placental tissue. Collagen produced from human fibroblast cell culture, or recombinantly-produced collagen expressed from a cell line may also be used.

Base (e.g., NaOH) is first added to HA to adjust the pH to 9-12. A cross-linker is added to the HA and the reaction is allowed to proceed. Collagen (pH 2-3) is then added. The collagen reacts with the cross-linker to covalently bind to HA. The cross-linker is consumed lightly in cross-linking the collagen. A HA solution is added as a lubricant and cross-linker scavenger. The final formulation has a core of cross-linked HA with collagen lightly cross-linked and surrounding the HA core. The additional soluble HA consumes the residual cross-linker and adds a lubrication benefit. Generally, any cross-linker that induces covalent bonds linking HA and collagen molecules may be used. Examples of such cross-linkers include but are not limited to VS, BDDE, ultraviolet radiation, gamma radiation, electron beam radiation, and glutaraldehyde.

Cross-linking of HA and collagen with VS is provided here as an example. Base is added to HA (30 mg/ml or higher) to raise the pH to 9-12. VS (500-10,000 ppm, and preferably 5000 ppm) is added. Cross-linking of HA by VS is allowed to proceed at an elevated temperature from 50° C. to 60° C. for about 1 hour. The cross-linked HA is cooled and acidic collagen (10-60 mg/ml, and preferably 30 mg/ml; pH 2-3) is added to bring the pH to ~7 (e.g., 6-8). The reaction is allowed to proceed overnight at room temperature. Soluble HA (3-15% weight/volume, and preferably 5-10% weight/volume) is added. Optionally, lidocaine can be added for a final lidocaine concentration of 2.7-3.3 mg/ml. The reaction is allowed to proceed for 8 hours-2 weeks at room temperature and pH 7.0-7.6. The scavenger HA not only decreases the amount of the residual VS but also functions as a coating agent which in turn reduces the extrusion force of the resulting implant (HAVSCgn). The HAVSCgn contains low residual VS (10 ppm or less) and has low extrusion force (e.g., 50 Newtons or less) through a fine gauge needle (>24 gaue). 5-50% amine groups on the collagen are modified by VS (i.e., loss of free amine groups) in the implant.

The HAVSCgn is a formulation with a high elastic modulus (>200 Pascals) yet low extrusion plateau. The elastic modulus (G') may be determined with a Bohlin Rheometer by measuring the ratio of the stress to the strain multiplied by the cosine of the phase angle. The extrusion force may be determined as follows: The implant is filled into a 1 cc Universal Syringe. A needle (e.g., 30G½ needle, Becton Dickinson Precision Glide) is then fit into the syringe and luer locked. The syringe filled with the implant and equipped with the needle is placed into the grip of Instron, Model 4201, and the plunger is displaced at a constant speed of 50 mm/minute. The force plateau is then calculated and reported in Newtons.

A cross-linked HA-collagen implant of the invention can be further homogenized and screened by forcing the formulation through a screen of defined pore size. The formulation can also be filled into syringes fitted with a #25 or larger gauge needle for injection. In the case of formulations used for dermal augmentation, the term "injectable" means that the formulation can be dispensed from syringes having a gauge as low as #25 under normal manual pressure with a smooth extrusion plateau.

The steps described above for preparing cross-linked HA-collagen and filling the implant into syringes are preferably carried out in sterile conditions using sterile materials.

The invention provides a soft tissue augmentation injectable that mimics the natural components of the skin. The composition of the present invention may be injected intradermally or subcutaneously to augment soft tissue and to repair or correct congenital anomalies, acquired defects, or cosmetic defects. Examples of such conditions include congenital anomalies such as hemifacial microsomia, malar and zygomatic hypoplasia, unilateral mammary hypoplasia, pectus excavatum, pectoralis agenesis (Poland's anomaly), and velopharyngeal incompetence secondary to cleft palate repair or submucous cleft palate (as a retropharyngeal implant); acquired defects (post traumatic, post surgical, or post infectious) such as depressed scars, subcutaneous atrophy (e.g., secondary to discoid lupis erythematosis), keratotic lesions, enopthalmos in the unucleated eye (also superior sulcus syndrome), acne pitting of the face, linear scleroderma with subcutaneous atrophy, saddle-nose deformity, Romberg's disease, and unilateral vocal cord paralysis; and cosmetic defects such as glabellar frown lines, deep nasolabial creases, circum-oral geographical wrinkles, sunken cheeks, and mammary hypoplasia.

The present invention provides a HA-collagen filler for augmenting and filling soft tissue defects and voids with a material that plumps and bulks the soft tissue. The cross-linked HA-collagen of the invention is particularly useful for deep dermal correction and sculpting. The superior composition and persistence makes it ideal for areas that are hard to correct and where a biocompatible bolus can provide mechanical strength to the body.

The following example is intended to illustrate, but not to limit, the scope of the invention. While such example is typical of those that might be used, other procedures known to those skilled in the art may alternatively be utilized. Indeed, those of ordinary skill in the art can readily envision and produce further embodiments, based on the teachings herein, without undue experimentation.

EXAMPLE

Preparation of HAVSCgn

HA was obtained from Lifecore Biomedical, Chaska, Minn. Base (NaOH) was added to HA to adjust the pH to a range of 9-12. Chemically pure VS (TCI AMERICA, 9211 N. Harborgate Street, Portland, Oreg. 97203, U.S.A) was then added to HA to allow the cross-linking reaction to proceed at an elevated temperature between 50° C. and 60° C. The cross-linked HA was cooled and collagen added.

Purified, type I, pepsin-digested human collagen was obtained from Inamed Biomaterials, 48490 Milmont Drive, Fremont, Calif. 94538. It was precipitated by raising the pH to 7.0-7.6 with a sodium phosphate solution and then centrifuging at 17000×g for 5-7 minutes. The supernatant was aseptically decanted from the centrifuge bottle. The collagen pellet was aseptically suctioned into a homogenization vessel and homogenized. 0.05 M HCl buffer and sterile filtered WFI (water for injection) were mixed with the homogenate to lower the final pH to 2-3.

The collagen was added to the cross-linked HA while the collagen was soluble. The VS was consumed and as a result the collagen was lightly cross-linked to collagen and HA. Additional HA in a solution was added at the end to consume the residual VS and to add a lubrication benefit. The final formulation had a core of cross-linked HA with collagen lightly cross-linked to the HA core. The additional HA was cross-linked to collagen and HA to enhance the formulation. The residual VS after addition of the free HA solution, as detected by reversed-phase HPLC, is indicated in Table 1.

TABLE 1

Consumption of Divinyl Sulfone

| Formulation | Residual Divinyl Sulfone |
| --- | --- |
| 30 mg/ml HA + 5000 ppm VS | 1776 ppm |
| 30 mg/ml HA + 5000 ppm VS + 5% HA solution | 18 ppm |
| 30 mg/ml HA + 5000 ppm VS + 10% HA solution | 0 ppm |

VS primarily reacts with the amine groups on collagen and the hydroxyl groups on HA. The percentage of modified amine groups on collagen was determined by a free amine assay using TNBS (trinitrobenzene sulfonate). Unmodified collagen was used as a control. The HAVSCgn, 2674-1, formulation had about 15% of the amine groups modified.

The reaction of VS with HA proceeds predominately with the hydroxyl groups of HA and the vinyl groups of VS and results in the formation of an ether bond.

(2) R—OH+CH2=CH—SO2—CH=CH2→R—O—CH2—CH2—SO2—CH2—CH2—O—R

Figure 4A:
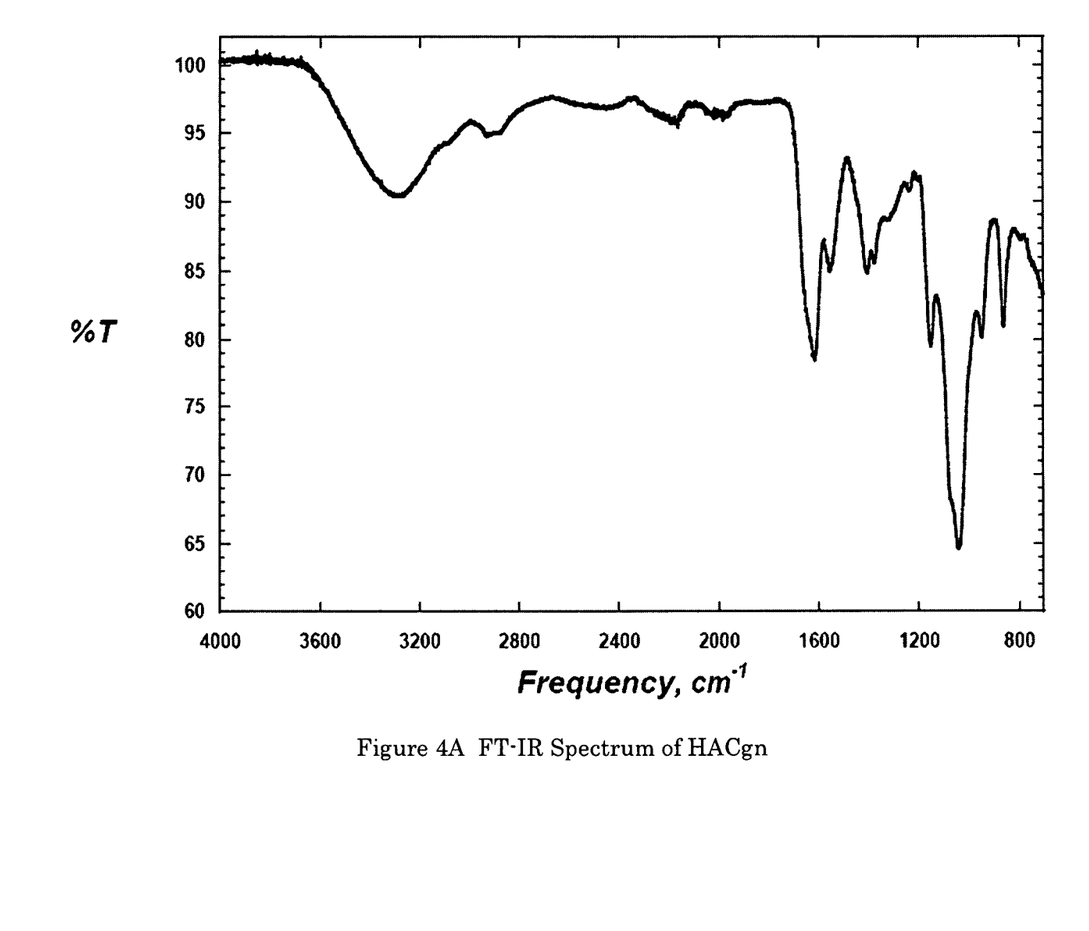
FIGS. 4A and 4B are FT-IR (fourier transform-infrared) traces for uncross-linked HACgn and cross-linked HAVSCgn, respectively.
Figure 4B:
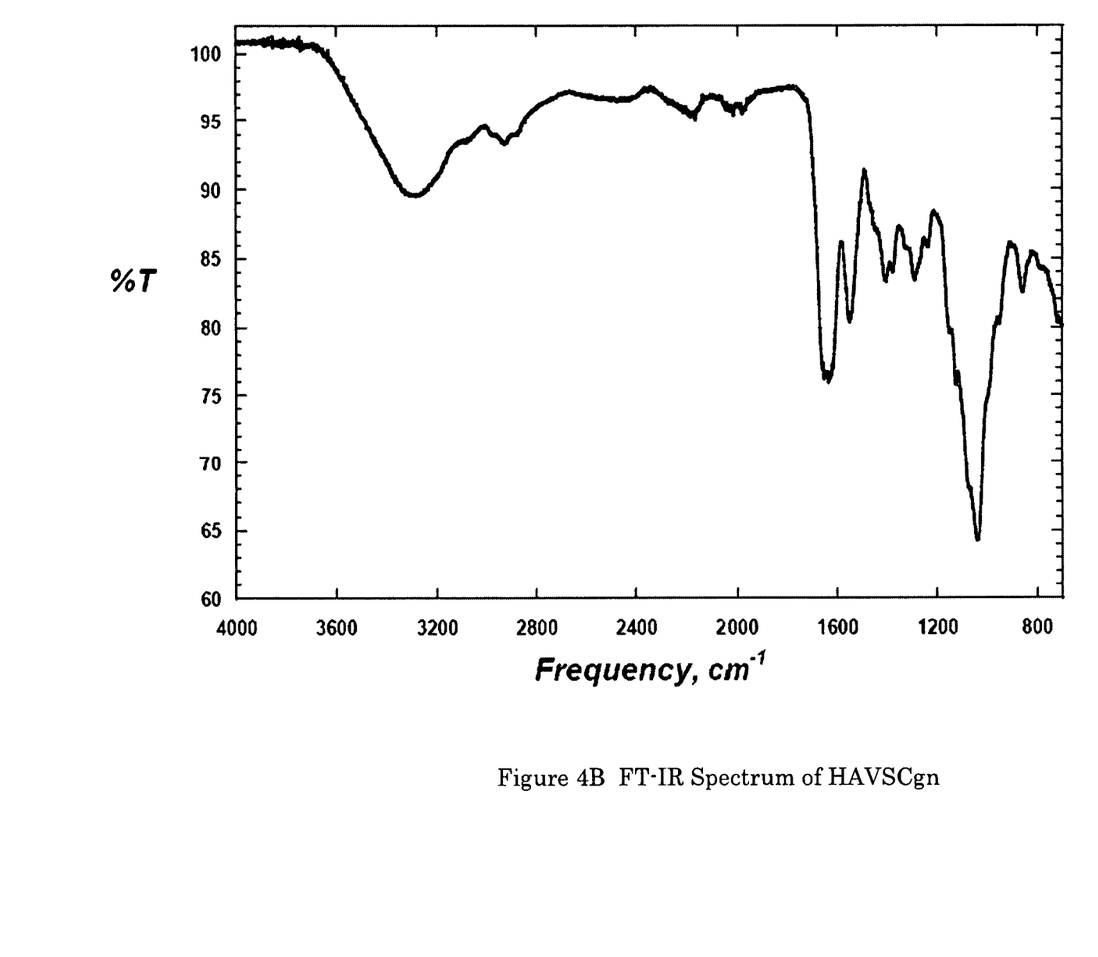

FIG. 4 shows FT-IR spectra obtained for uncross-linked HACgn (a mixture of uncross-linked HA and uncross-linked collagen) and the HAVSCgn formulation. The representative absorption peaks in both samples were assigned to primary amines at 3500-3300 cm$^{-1}$ and alcohol or OH groups at 3650-3200 cm$^{-1}$ which overlaps the ether bond at 1300 cm$^{-1}$. Cross-linked HAVSCgn had an ether peak whereas the uncross-linked sample did not have a peak at 1300 cm$^{-1}$.

Rheology of HAVSCgn

Figure 1:
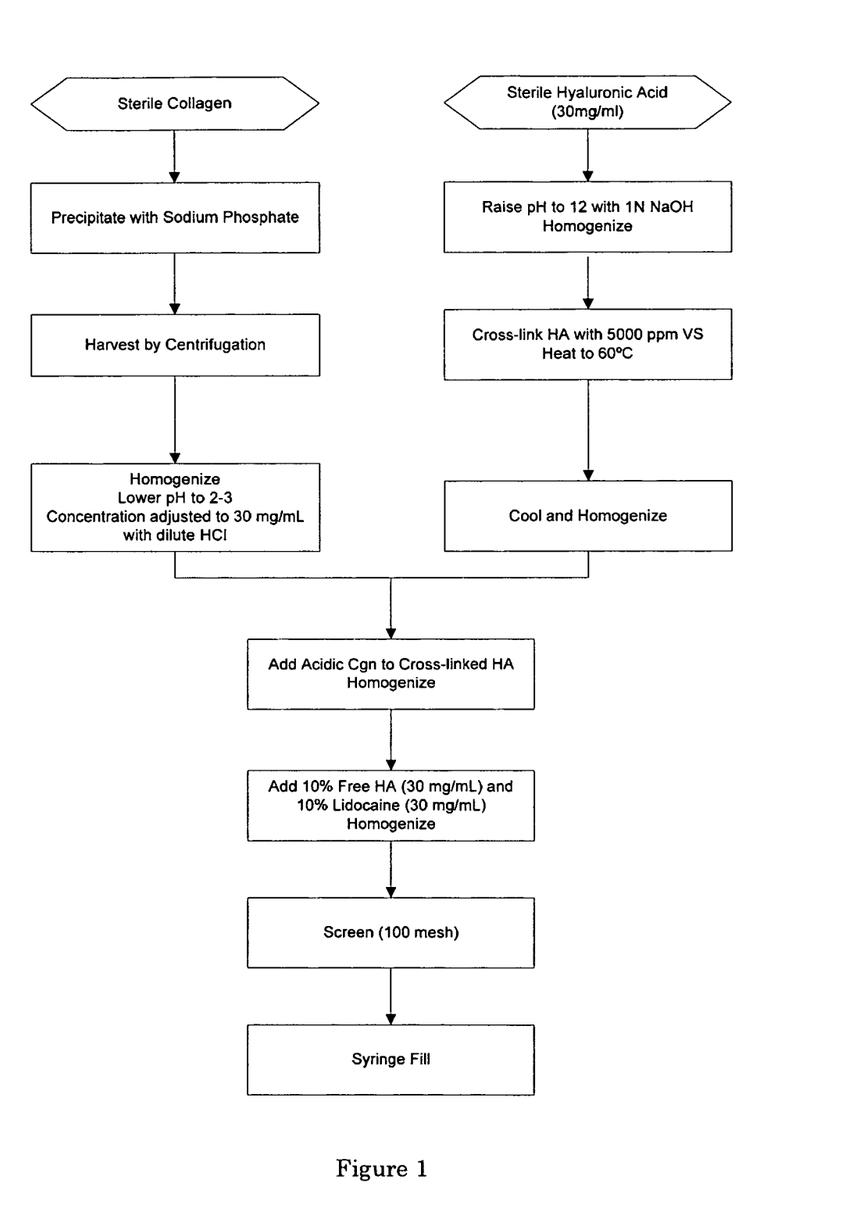
FIG. 1 is a flow chart illustrating a representative process for HAVSCgn preparation.
Figure 2:
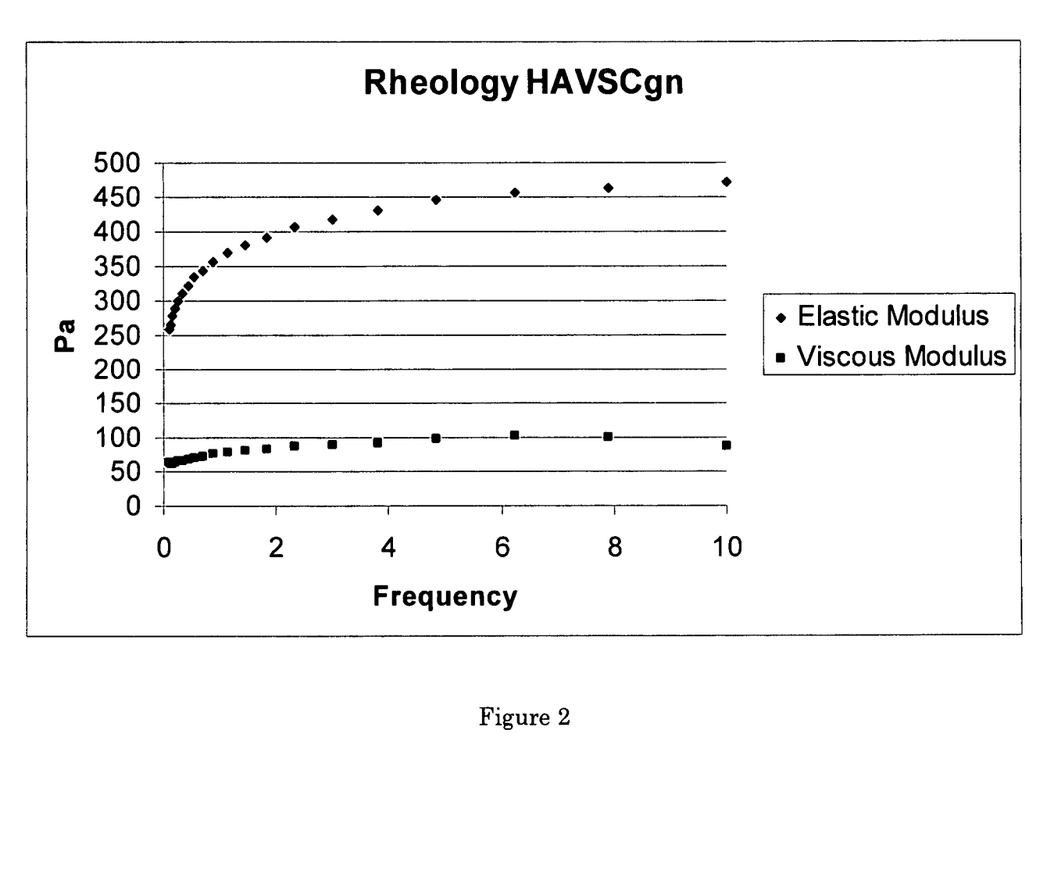
FIG. 2 shows elastic and viscous modulus during a frequency sweep of HAVSCgn.

FIG. 2 shows a frequency sweep test using a Bohlin Rheometer to determine the elastic modulus (G') and the viscous modulus (G") of HAVSCgn. The elastic modulus reflects the elasticity of a material, and indicates the strength and stability of the HAVSCgn three-dimensional structure. Stability of the three-dimensional structure refers to the ability of HAVSCgn to resist deformation to maintain a three-dimensional form. The higher the value of G' at a given frequency, the more elastic the HAVSCgn will be. The viscous modulus reflects the viscosity of a material. The higher the value of G" at a given frequency, the more viscous the HAVSCgn gel composition will be.

Enzyme Resistance

Figure 3:
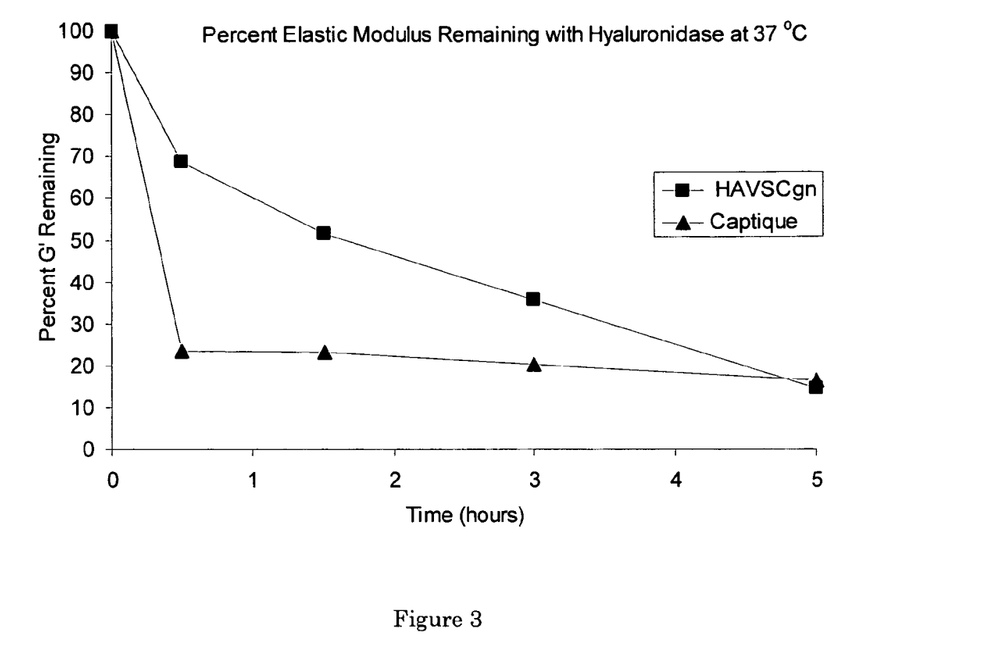
FIG. 3 depicts effects of hyaluronidase (enzymatic) degradation of HAVSCgn relative to Captique™ on the elastic modulus.

Hyaluronidase effect on elastic modulus was studied for HAVSCgn and Captique™ (a formulation of HA cross-linked with VS). Hyaluronidase was obtained from Worthington Biochemical Corporation (730 Vassar Avenue, Lakewood, N.J. 08701; catalog number L5002592). Implants were weighed to about 2±0.1 gram. 5 mg hyaluronidase was diluted with 10 ml PBS solution to ~50 U/ml. 0.020 ml hyaluronidase solution was added to each 2 gram implant sample. The samples were incubated at 37° C. for 30 minutes, 1.5 hours, 3 hours, and 5 hours. The elastic modulus and phase angle were tested at 5 Hz using a Bohlin Rheometer CVO-100 at 20° C. with a gap of 500 mm and a parallel plate (PP20). As shown in FIG. 3, HAVSCgn was more resistant to hyaluronidase than Captique™.

Biocompatability

The biocompatibility of HAVSCgn was tested and demonstrated to be biocompatible. The safety of the HAVSCgn was assessed through a cytotoxicity study and multiple rabbit subcutaneous implantation studies. The cytotoxicity study was performed using the ISO Elution Method. As shown in Table 2, HAVSCgn caused no cell lysis or toxicity.

TABLE 2

Cytotoxicity of HAVSCgn

| Test | Score |
| --- | --- |
| Confluent monolayer | 0 |
| Percent rounding | 0 |
| Percent cells without intrascytoplasmic granules | 0 |
| Percent lysis | 0 |
| Grade | 0 |
| Reactivity | None |

A rat subcutaneous implantation study was performed to determine the persistence of HAVSCgn. As part of the rat implantation study, a macroscopic evaluation of the implant site was performed. There was no capsule formation or adverse reaction for all time points studied (Table 3).

TABLE 3

Rat Subcutaneous Gross and Microscopic Evaluations

| Time Point | HAVSCgn |
| --- | --- |
| 4 weeks | No capsule formation or adverse reaction. Non irritant. |
| 9 weeks | No capsule formation or adverse reaction. Non irritant. |
| 13 weeks | No capsule formation or adverse reaction. Non irritant. |
| 24 weeks | No capsule formation or adverse reaction. Non irritant. |

Effectiveness

Figure 5:
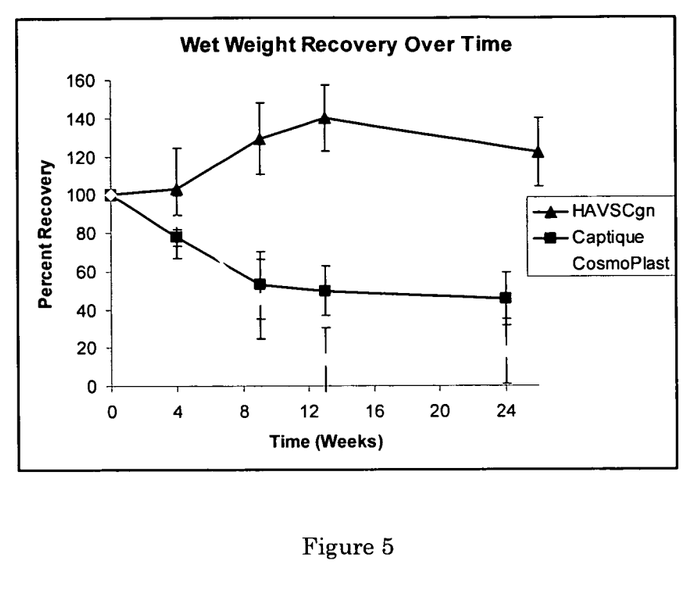
FIG. 5 shows persistence of HAVSCgn relative to Captique™ and CosmoPlast®.

To assess effectiveness, the persistence of HAVSCgn (2674-1) relative to CosmoPlast® and Captique™ was evaluated using wet weight recovery in the rat subcutaneous model which is considered to be a good measure of an implant's ability to maintain wrinkle correction (McPherson et al., 1988, Development and Biochemical Characterization of Injectable Collagen, *J Dermatol Surg Oncol* 14, Suppl 1). As shown in FIG. 5, HAVSCgn had greater wet weight recovery than CosmoPlast® and Captique™ after implantation.

All patents and articles cited herein are incorporated by reference in their entirety.

What is claimed is:

1. A method for preparing a tri-layer composition, the method comprising the steps of:
   a) forming a first composition by contacting hyaluronic acid (HA) solution comprising HA and having a pH of about 9 to about 12 with a cross-linker to allow cross-linking of the HA by the cross-linker;
   b) homogenizing the first composition;
   c) forming a second composition by contacting the first composition with collagen solution comprising collagen and having a pH of about 2 to about 3 to allow cross-linking of the collagen by the cross-linker to the first composition, wherein the second composition has a cross-linked HA core with a layer of collagen surrounding and cross-linked to the cross-linked HA core; and
   d) forming a tri-layer composition by contacting the second composition with a HA in a solution comprising HA and having a pH of about 6 to about 8 to allow cross-linking of the HA by the cross-linker to the second composition, wherein the tri-layer composition has a cross-linked HA core, a middle layer of collagen layer surrounding and cross-linked to the cross-linked HA core, and an outer layer of HA surrounding and cross-linked to the middle layer of collagen.

2. The method of claim 1, wherein in step (a) the cross-linker is divinyl sulfone (VS) or 1,4-butanediol diglycidyl ether (BDDE).

3. The method of claim 2, wherein the concentration of the VS for forming the first composition is about 500-10,000 ppm.

4. The method of claim 3, wherein the concentration of the VS for forming the first composition is about 5000 ppm.

5. The method of claim 2, wherein the cross-linking of the HA by the VS for forming the first composition occurs at about 50-60° C.

6. The method of claim 1, wherein in step (a) the concentration of HA in the HA solution for forming the first composition is about 30 mg/ml or higher.

7. The method of claim 1, wherein in step (b) the concentration of collagen in the collagen solution for contacting the first composition is about 10-50 mg/ml.

8. The method of claim 7, wherein the concentration of the collagen for contacting the first composition is about 30 mg/ml.

9. The method of claim 1, wherein in step (b) the collagen in the collagen solution for contacting the first composition is a collagen type I, II, III, IV, or V, or a combination thereof.

10. The method of claim 1, wherein in step (b) contacting of the first composition with collagen solution results in the second composition having a pH of about 6-8.

11. The method of claim 10, wherein the second composition has a pH of about 7.

12. The method of claim 1, wherein in step (c) the concentration of the HA in the HA solution for contacting the second composition is about 3-15% weight/volume.

13. The method of claim 12, wherein in step (c) the concentration of the HA in the HA solution for contacting the second composition is about 5-10% weight/volume.

14. The method of claim 1, wherein in step (c) the HA solution has a pH of about 7.0-7.6.

15. The method of claim 1, wherein step (b) further comprises contacting the second composition with a local anesthetic agent.

16. The method of claim 15, wherein the local anesthetic agent is lidocaine.

17. The method of claim 16, wherein the concentration of the lidocaine in the implant is about 1-7 mg/ml.

18. The method of claim 17, wherein the concentration of the lidocaine in the implant is about 2.7-3.3 mg/ml.

19. An implant prepared according to the method of claim 1.

20. A packaged product, comprising a syringe and a needle, wherein the syringe is loaded with the implant of claim 19.

21. A method for filling voids and defects and increasing tissue volume in a mammal, comprising administering to a mammal the implant of claim 19.

22. The method of claim 21, wherein the implant is administered by intradermal or subcutaneous injection.

23. A tri-layer implant, comprising:
   a) a core of cross-linked HA;
   b) a middle layer of collagen surrounding and cross-linked to the core of cross-linked HA; and
   c) an outer layer of HA surrounding and cross-linked to the middle layer of collagen;
      wherein the tri-layer implant is more resistant to hyaluronidase degradation than a single-layer implant comprised of HA.

24. The implant of claim 23, wherein about 5-50% of the amine groups on the collagen are cross-linked to the core of cross-linked HA.

25. The implant of claim 23, wherein the elastic modulus of the implant is higher than about 200 Pascals.

26. The implant of claim 23, wherein the implant has an extrusion force through a 24 or larger gauge needle of about 50 Newtons or less.

27. The implant of claim 23, further comprising a local anesthetic agent.

28. The implant of claim 27, wherein the local anesthetic agent is lidocaine.

29. The implant of claim 28, wherein the concentration of the lidocaine in the implant is about 1-7 mg/ml.

30. The implant of claim 29, wherein the concentration of the lidocaine in the implant is about 2.7-3.3 mg/ml.

* * * * *

UNITED STATES PATENT AND TRADEMARK OFFICE
CERTIFICATE OF CORRECTION

PATENT NO. : 8,697,044 B2
APPLICATION NO. : 12/247175
DATED : April 15, 2014
INVENTOR(S) : Jacqueline A. Schroeder et al.

It is certified that error appears in the above-identified patent and that said Letters Patent is hereby corrected as shown below:

On the title page, in item (56), under "Other Publications", in column 2, line 2, delete "Stardards," and insert -- Standards, --, therefor, On the title page, in item (56), under "Other Publications", in column 2, line 7, delete "comosite" and insert -- composite --, therefor.

On title page 3, in column 2, under "Other Publications", line 7, delete "(JUVADERM)" and insert -- (JUVEDERM) --, therefor.

On title page 3, in column 2, under "Other Publications", line 24, delete "Chrondrocytes" and insert -- Chondrocytes --, therefor.

On title page 3, in column 2, under "Other Publications", line 30, delete "Gonarthosis:" and insert -- Gonarthrosis: --, therefor.

On title page 3, in column 2, under "Other Publications", line 66, delete "Rheuymatism;" and insert -- Rheumatism; --, therefor.

On title page 4, in column 1, under "Other Publications", line 17, delete "Influcence" and insert -- Influence --, therefor.

On title page 4, in column 1, under "Other Publications", line 18, delete "Chemcio-" and insert -- Chemico- --, therefor.

On title page 4, in column 1, under "Other Publications", line 24, delete "Crosslinkedwith" and insert -- Crosslinked with --, therefor.

On title page 4, in column 1, under "Other Publications", lines 24-25, delete "Glyol Tetracrylates";" and insert -- Glycol Tetraacrylate"; --, therefor.

On title page 4, in column 1, under "Other Publications", line 33, delete ""Characerization" and insert -- "Characterization --, therefor.

Signed and Sealed this
Twenty-sixth Day of May, 2015

Michelle K. Lee
*Director of the United States Patent and Trademark Office*

CERTIFICATE OF CORRECTION (continued)
U.S. Pat. No. 8,697,044 B2

On title page 4, in column 1, under "Other Publications", line 37, delete ""Hyroxyethyl" and insert -- "Hydroxyethyl --, therefor.

On title page 4, in column 2, under "Other Publications", line 37, delete "Institue" and insert -- Institute --, therefor.

On title page 4, in column 2, under "Other Publications", line 39, delete "Slerotomy" and insert -- Sclerotomy --, therefor.

On title page 5, in column 1, under "Other Publications", line 8, delete "Viscoelstic" and insert -- Viscoelastic --, therefor.

In the Specification

In column 3, line 64, delete "(10-60" and insert -- (10-50 --, therefor.

In column 4, line 9, delete "gaue)." and insert -- gauge). --, therefor.

In column 4, line 49, delete "lupis" and insert -- lupus --, therefor.

In column 4, line 50, delete "enopthalmos" and insert -- enophthalmos --, therefor.

In column 4, line 50, delete "unucleated" and insert -- enucleated --, therefor.

In column 6, line 26, delete "Biocompatability" and insert -- Biocompatibility --, therefor.

In column 6, line 39, delete "intrascytoplasmic" and insert -- intracytoplasmic --, therefor.